(12) United States Patent
Titterton

(10) Patent No.: US 7,334,457 B2
(45) Date of Patent: Feb. 26, 2008

(54) MULTI-CAPILLARY VISCOMETER SYSTEM AND METHOD

(75) Inventor: Alan Titterton, Yarm (GB)

(73) Assignee: Viscotek Corporation, Houston, TX (US)

( * ) Notice: Subject to any disclaimer, the term of this patent is extended or adjusted under 35 U.S.C. 154(b) by 0 days.

(21) Appl. No.: 11/249,839

(22) Filed: Oct. 12, 2005

(65) Prior Publication Data

US 2007/0079659 A1    Apr. 12, 2007

(51) Int. Cl.
*G01N 11/08* (2006.01)
(52) U.S. Cl. .................. 73/54.06; 73/54.04
(58) Field of Classification Search ........... 73/54.04, 73/54.06
See application file for complete search history.

(56) References Cited

U.S. PATENT DOCUMENTS

| | | | | |
|---|---|---|---|---|
| 4,578,990 A * | 4/1986 | Abbott et al. | ............. | 73/54.06 |
| 4,627,271 A * | 12/1986 | Abbott et al. | ............. | 73/54.06 |
| 6,708,553 B2 * | 3/2004 | Bures | ............. | 73/54.04 |
| 6,712,085 B2 * | 3/2004 | Weissgerber et al. | ......... | 137/12 |
| 6,877,361 B2 * | 4/2005 | Bures | ............. | 73/54.04 |
| 2002/0166367 A1 * | 11/2002 | Bures | ............. | 73/54.04 |
| 2004/0134262 A1 * | 7/2004 | Bures | ............. | 73/54.05 |

* cited by examiner

*Primary Examiner*—Andre J. Allen
(74) *Attorney, Agent, or Firm*—The Matthews Firm

(57) ABSTRACT

This apparatus and method relates to the improved sensing of fluid differential pressures. The apparatus and method can be applied in multi-capillary solution viscometers and gel permeation chromatography systems used in the characterization of polymers. A valve is used to alter a flow path in a measurement circuit to reduce or eliminate an undesired fluid output and to accelerate the regeneration of the fluid for analysis of subsequent samples. The apparatus and method can be usefully applied to all instruments and systems comprising viscometers having two or more capillaries.

29 Claims, 7 Drawing Sheets

MULTI-CAPILLARY VISCOMETER SYSTEM AND METHOD

FIELD OF THE INVENTION

The present invention relates to multi-capillary viscometers used to measure and analyze the viscosity of a sample solution. The viscosity analysis circuit may be used in conjunction with Gel Permeation Chromatography ("GPC") or Size Exclusion Chromatography ("SEC") to determine other properties of the sample such as molecular size or weight distributions.

DETAILED DESCRIPTION OF THE EMBODIMENTS

For a further understanding of the nature, function, and objects of the present invention, reference should now be made to the following detailed description taken in conjunction with the accompanying drawings. Detailed descriptions of embodiments of the apparatus are provided herein, as well as a mode of carrying out and employing embodiments of the present apparatus. It is to be understood, however, that the present apparatus may be embodied in various forms. The description provided herein relates to the common components of 'sample capillary', 'delay volume component(s)', 'reference capillary' and 'diverter valve' which may form only part of a more complex circuit. Therefore, specific details disclosed herein are not to be interpreted as limiting, but rather as a basis for the claims and as a representative basis for teaching one skilled in the art to employ the present embodiments of one form of the apparatus in virtually any appropriately detailed system, structure, or manner. The embodiments described herein are considered illustrative of both the processes taught by the described embodiments of products and articles of manufacture yielded in accordance with the present embodiments of one form of the apparatus. The inventive device and method can be used in a multi-capillary viscometer for which the basic operating principles are disclosed in U.S. Pat. No. 4,463,598 (Haney), in U.S. Pat. Nos. 4,627,271 and 4,578,990 (Abbott, et al), and in U.S. Pat. No. 5,637,790 (De Corral).

In the prior art, multi-capillary viscometers are constructed and operated such that a reference flow of solvent may be maintained during a measurement by inserting a 'delay volume component' in front of a 'reference capillary'. The 'delay volume component' initially contains pure solvent at the beginning of the analysis. It provides a continuing flow of solvent to a 'reference capillary' while sample flows though a 'sample capillary'. A limitation of such prior art multi-capillary viscometers, whether used only for viscosity measurements or in combination with other detectors in GPC or SEC analysis, is what is typically referred to as a 'breakthrough peak', being an unwanted instrument response resulting from the discharge of sample fluid from the 'delay volume component' through a 'reference capillary' after pressure readings useful in determining information about the viscosity of the sample have been taken. The 'breakthrough peak' can last for a substantial period of time after the measurement process is completed because the delay volume spreads the peak, thereby delaying measurement of the next sample.

Figure 1:
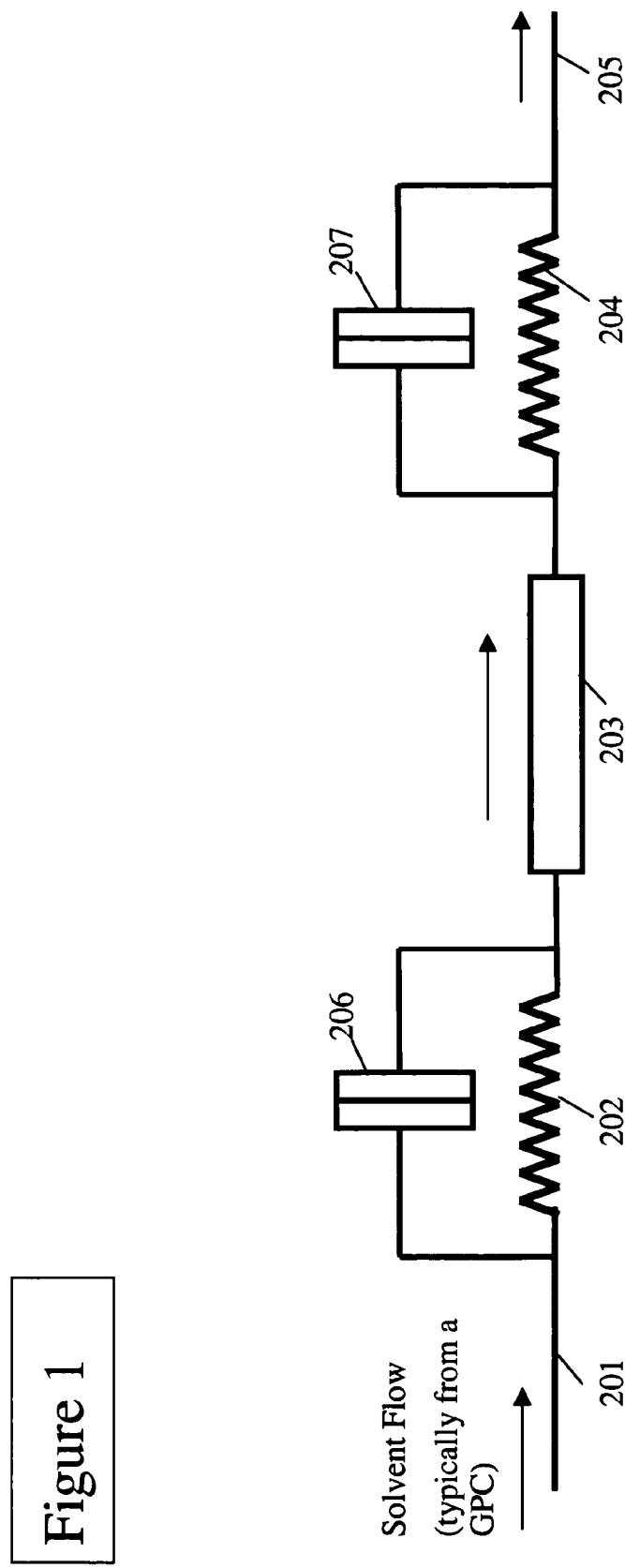
FIG. 1 illustrates a schematic view of a general multi-capillary viscometer.

The cause of the 'breakthrough peak' effect can be appreciated by reference to FIG. 1 accompanied with the following description:

FIG. 1 illustrates schematically a simple multi-capillary viscometer and the way in which it operates. The operating 'circuit' consists of an inlet tube (201) coupled in series to a narrower bore capillary tube (202) referred to as the 'sample capillary', a 'delay volume component' (203) which has a hold-up volume of significantly large capacity, a second narrow bore capillary tube (204) referred to as the 'reference capillary', and finally an exit pipe (205). When a fluid such as a solvent is pumped through the circuit, a differential pressure will be generated, mainly across the capillary tubes since they have a narrower cross-sectional area than the connecting tubing and other components in the circuit. The pressure across each capillary may be monitored continuously by means of a suitable transducer (206) (207). A sample solution is injected into the flowing solvent stream and is carried through the circuit. Its passage through the 'sample capillary' (202) will typically cause an increased pressure drop because of the viscosity of the sample and be detected by the transducer (206) across that capillary. However the pressure monitored by the transducer (207) across the 'reference capillary' (204) will remain substantially unaltered since it will still be receiving solvent eluting from the 'delay volume component' (203). The relative viscosity may be mathematically derived using the ratio of the pressure drop across the sample capillary (202) to the pressure drop across the reference capillary (204) as described in, for example, Abbott, et al. The relative viscosity will increase as sample flows into the viscometer.

The volume of the 'delay volume component' is selected to be sufficient to supply the 'reference capillary' (204) with solvent during the measurement process. Eventually all the sample solution will emerge from the 'sample capillary' (202) and enter the 'delay volume component' (203). The pressure across the 'sample capillary' (202) will return to the baseline value and the useful part of the measurement cycle is over. However, the sample will eventually progress all the way through the 'delay volume component' (203) and enter the 'reference capillary' (204) where it will cause a rise in pressure, measured by the transducer (207). This increase in pressure in turn causes a decrease in the measured relative viscosity, which is the cause of the 'breakthrough peak'.

Figure 2A:
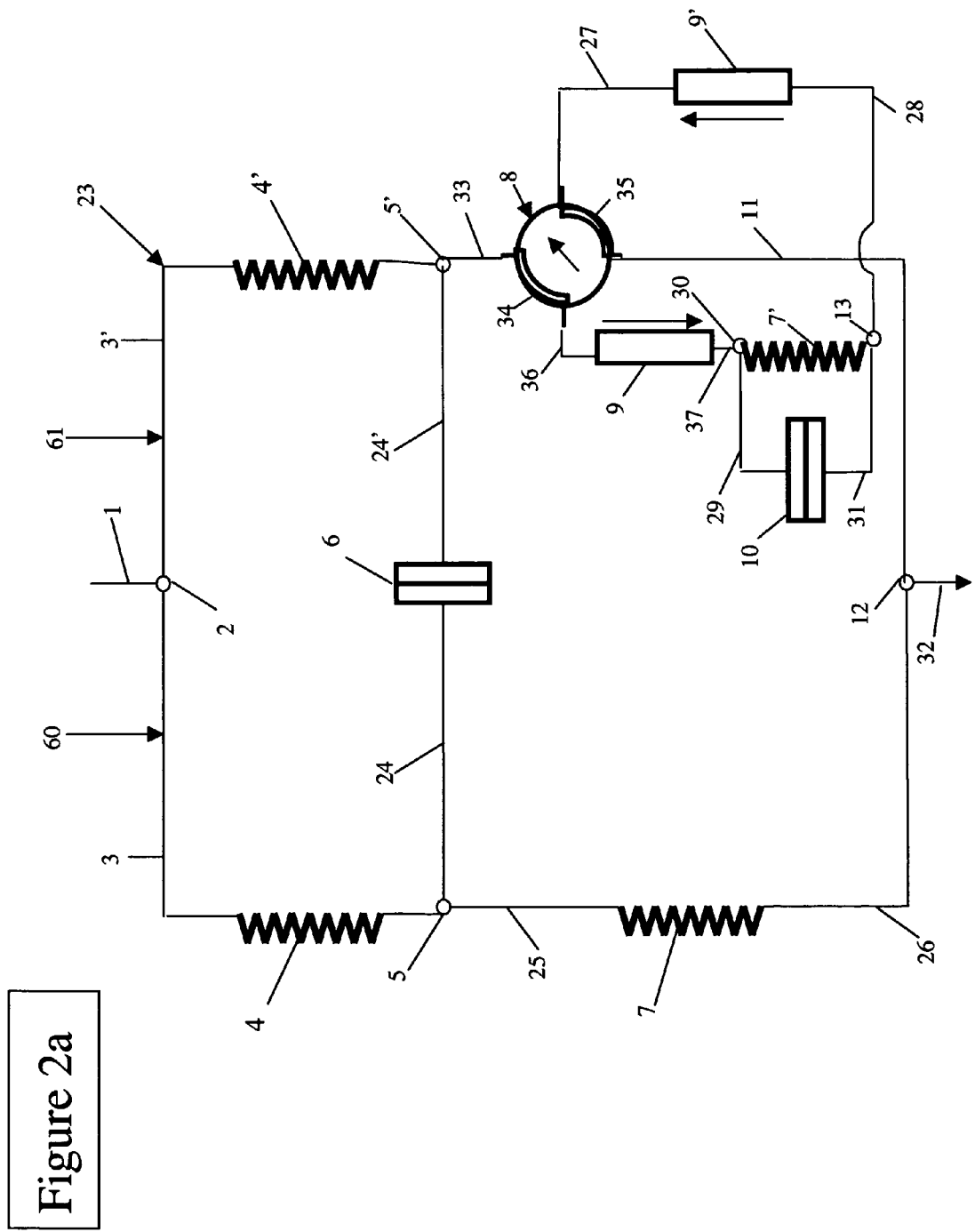
FIG. 2a illustrates a block diagram of one embodiment of the apparatus with two delay volume components and a fluid diverting component in orientation 'A'

FIG. 2a illustrates one embodiment of the present embodiments of one form of the apparatus comprising a fluid viscosity measurement circuit 23 having components connected together preferably using conventional tubing connectors, fittings or unions and connecting tubing. The fluid viscosity measurement circuit 23 preferably has a fluid insertion or injection tube 1 through which a fluid is inserted. Fluid viscosity measurement circuit 23 preferably has a first fluid flow circuit 60 and a second fluid flow circuit 61.

In the embodiment illustrated by FIG. 2a, the fluid insertion or injection tube 1 attaches to a split junction 2, which can include but is not limited to a T-bridge split junction. The split junction 2 is attached to two lengths of pipe or tubing 3 and 3'. The two lengths of pipe or tubing 3 and 3' are attached to the split junction 2 so as to allow a fluid to move through the split junction 2 into length of pipe or tubing 3 and length of pipe or tubing 3'. A length of pipe or tubing 3 is connected between the split junction 2 and a capillary 4. Capillary 4 is preferably a conventional fluid capillary, which is preferably a tube, having a relatively small inside diameter (typically, but not limited to, the range of about 0.009" to 0.014") in comparison to the relatively large inside diameter of other fluid components in the circuit (typically, but not limited to, 0.04" or more for connecting tubing and fittings and 0.062" or more for delay volumes), that serves to provide a flow restriction within the fluid viscosity measurement circuit. "Capillaries" or "capillary" are defined throughout this application to include any structure with a cross-sectional hollow portion having a relatively small inside diameter to produce a pressure drop higher than that produced by other individual components of the fluid viscosity measurement circuit.

The length of pipe or tubing 3' is connected between the split junction 2 and a capillary 4'. Capillaries 4 and 4' are preferably conventional fluid capillaries. Capillary 4 is preferably connected to a second split junction 5. Capillary 4' is preferably connected to a second split junction 5'. Split junction 5 and split junction 5' are preferably connected to transducer tubes or lines 24 and 24' respectively. Transducer tubes or lines 24 and 24' are preferably connected to split junctions 5 and 5' respectively and to a transducer 6 in a conventional fashion. "Transducer" or "transducers" are defined throughout this application to include any structure or apparatus operable for sensing or measuring fluid differential pressures and are preferably differential pressure transducers of the type described in Abbot, et al and De Coral wherein two cavities are separated by a diaphragm which is deflected by a pressure difference in the cavities to produce an electrical signal proportional to the pressure differential.

Transducer 6, and all transducers referred to herein, are preferably connected in a "dead-end" manner as described in FIG. 1c, such that only the inlet ports of the transducers remain open after the transducer lines and cavities are filled and purged for operation, and pressure is transmitted by static fluid in the transducer lines and cavities to the transducer diaphragm. Transducer 6 and all transducers referred to herein may also be connected in a "flow-through" manner, as described in FIG. 1d wherein inlet and outlet (or purge) ports of each cavity of the transducer are connected such that fluid flowing through one or more of the other components in the circuit also flows through the transducer cavities, and fluid pressure is transmitted to the transducer diaphragm by the fluid flowing through the transducer cavities.

Split junction 5 preferably connects to fluid tube 25. Fluid tube 25 preferably connects to capillary 7. Capillary 7 preferably connects to fluid tube 26. Fluid tube 26 preferably connects to split junction 12. Split junction 12 preferably connects to fluid tube 32.

Split junction 5' preferably connects to fluid tube 33. Fluid tube 33 preferably connects to fluid path diverter valve 8. Fluid path diverter valve 8 preferably contains a plurality of fluid pathways 34 and 35. "Diverter valve" or "valve" as defined in this application refers to any valve or structure operable to selectively direct or align the flow of fluid from one fluid pathway to another and may include, but is not limited to, a valve operable for that purpose in a prescribed or automated fashion, which may be, but is not limited to, electrical, pneumatic or timed operation or activation. "Diverter valve" as defined in this application can be, but is not limited to a 4-port, 2 position plug valve, such as Hamilton HV-86779. As shown in FIG. 2a fluid pathway 34 is preferably connected to fluid tube 36 and fluid pathway 35 is preferably connected to fluid tube 27. Fluid tube 36 is preferably connected to delay volume 9. Delay volume 9 is preferably connected to fluid tube 37. "Delay volume" is defined in this application to include any means of delaying a fluid's arrival at another point in the fluid circuit, which may include, but is not limited to, increased volume tubing or reservoirs. A typical delay volume can include, but is not limited to a packed column. Fluid tube 37 is preferably connected to split junction 30. Capillary 7' is also preferably connected to split junction 30. Capillary 7' can be, but is not necessarily, substantially identical to capillary 7. Transducer line or tube 29 is also preferably attached to split junction 30.

Transducer line or tube 29 is preferably connected to a transducer 10. Transducer 10 is preferably a conventional transducer utilized in measuring fluid viscosity. Transducer 10 is preferably connected in the "dead-end" manner described above for transducer 6. Transducer 10 and transducer 6 are preferably substantially identical. Transducer 10 is also preferably connected to transducer line or tube 31 such that the connections of transducer line or tube 29 and transducer line or tube 31 are on substantially opposite sides of the transducer diaphragm. Transducer line or tube 31 is preferably connected to the split junction 13. Capillary 7' is likewise preferably connected to the split junction 13. Fluid tube line 28 is preferably connected to split junction 13 and to a delay volume 9'. Delay volume 9 and delay volume 9' are preferably substantially identical. Delay volume 9' is preferably connected on its opposite end to fluid tube 27. Fluid tube 27 is preferably connected to fluid pathway 35 at fluid path diverter valve 8. Fluid pathway 35 is also preferably connected on its opposite end to fluid tube 11. Fluid tube 11 is preferably connected to split junction 12.

Figure 2B:
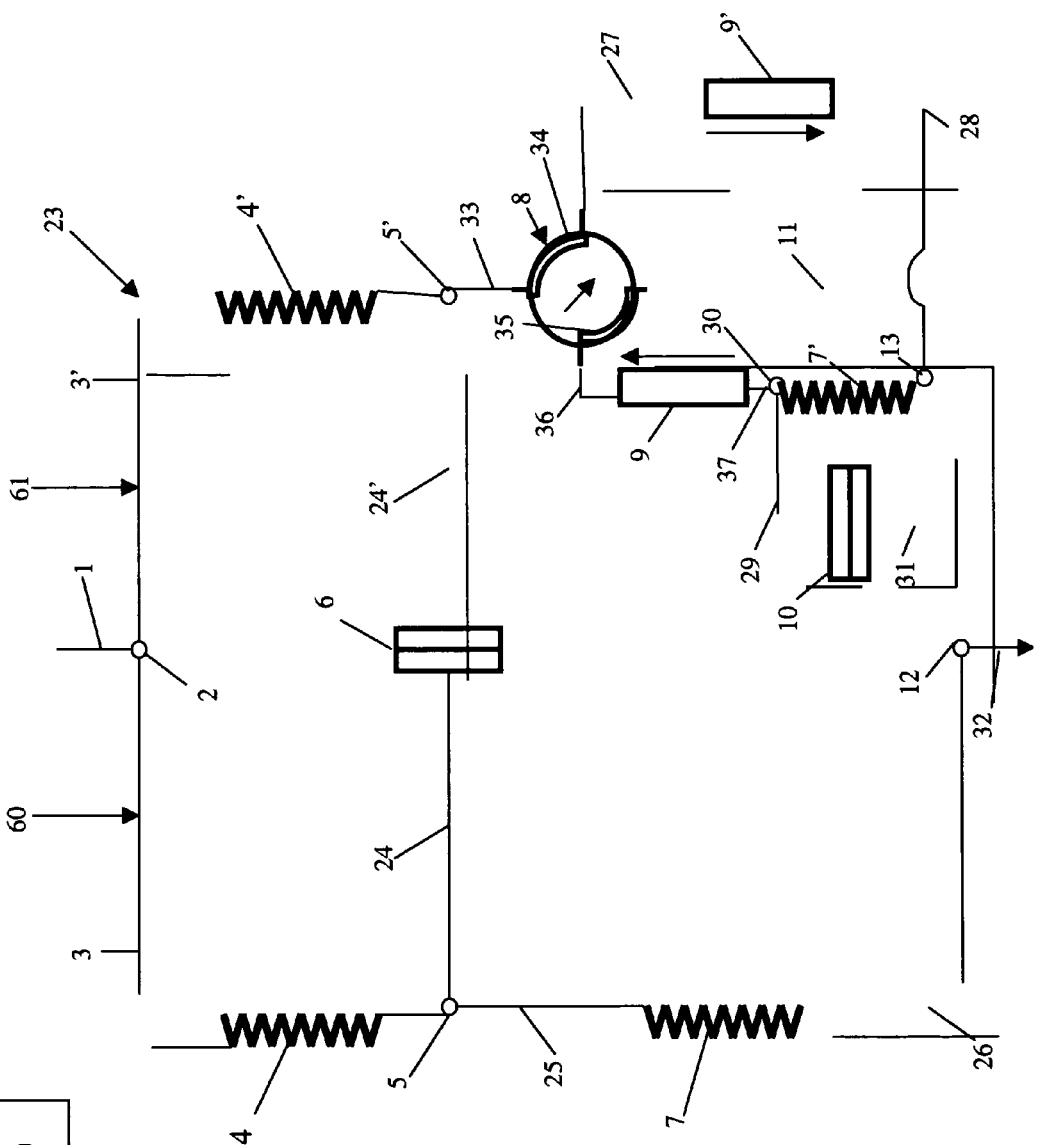
FIG. 2b illustrates a block diagram of one embodiment of the apparatus with two delay volume components and a fluid diverting component in orientation 'B'

FIG. 2b, illustrates one embodiment of the present embodiments of one form of the apparatus and is substantially identical to FIG. 2a, except in FIG. 2b, fluid path diverter valve 8 is positioned such that fluid pathway 34 is aligned between fluid tubes 33 and 27, and fluid pathway 35 is aligned between fluid tubes 11 and 36.

The embodiment of the apparatus as disclosed in FIG. 2a operates in, but is not limited to, substantially the following manner. When in pre-sample testing mode, a stream of reference fluid or solvent runs through the system and follows one of a plurality of pathways. As the solvent flows into the system through fluid tube 1, it moves until it approaches split junction 2, at which point the fluid stream splits to flow into both fluid tubes 3 and 3'. The solvent then flows through capillaries 4 and 4' and approaches split junctions 5 and 5' respectively. The fluid pressure at split junctions 5 and 5' respectively is transmitted by the fluid in transducer tubes or lines 24 and 24' to opposite sides of transducer 6. The fluid that flows into fluid tube 25 proceeds to flow through capillary 7, through fluid tube 26 and then to split junction 12. The fluid that flows from fluid tube 33 flows into fluid pathway 34. It then flows into fluid tube 36 and then into an delay volume 9. The fluid stream then flows into a fluid tube 37, which connects to a split junction 30, and then into capillary 7'. The fluid pressure at split junction 30 is transmitted by the fluid in transducer line or tube 29 to one side of transducer 10. The fluid entering split junction 30 from delay volume 9 flows through capillary 7' to split junction 13. The pressure of the fluid at split junction 13 is transmitted by the fluid in transducer line or tube 31 to one side of transducer 10, thus enabling the transducer to produce a signal substantially corresponding to the differential pressure across capillary 7' (the difference in fluid pressures upstream and downstream capillary 7'.) The fluid flow, when it reaches split junction 13, flows into fluid tube 28, then into delay volume 9' and then into fluid tube 27. The fluid then flows into fluid pathway 35 and then into fluid tube 11. The fluid then flows into split junction 12. The fluids in pathways along fluid tube 26 and fluid tube 11 meet at split junction 12, then exit out fluid tube 32 which is connected to split junction 12. Reference fluid may be flowed continuously through the measurement circuit to allow base line readings to be developed from transducers 6 and 10 with the measurement circuit full of flowing reference fluid.

With fluid diverter valve 8 positioned as disclosed in FIG. 2b, the measurement circuit operates in substantially the same manner as described in FIG. 2a. The fluid flowing from tube 33 flows into fluid pathway 34 and then into fluid tube 27. The fluid then enters delay volume 9' and flows into fluid tube 28. The fluid then flows into split junction 13 connecting transducer line or tube 31 and capillary 7'. The pressure of the fluid at split junction 13 is transmitted by the fluid in transducer line or tube 31 to one side of transducer 10. The fluid that flows through capillary 7' enters split junction 30 and then into fluid tube 37. The pressure of the fluid at split junction 30 is transmitted by the fluid in transducer line or tube 29 to one side of transducer 10. The fluid exiting fluid tube 37 flows into a delay volume 9. The fluid then flows from the delay volume 9 into fluid tube 36, which is connected to fluid pathway 35. The fluid flows into fluid pathway 35, which is connected to fluid tube 11 and then to split junction 12.

To measure the viscosity of a sample fluid with the viscosity measurement circuit as per FIG. 2a, the sample is preferably injected or added into the reference fluid at or upstream of the inlet to the measurement circuit at tube 1. The sample then flows in solution with the reference fluid along the same fluid pathway as described above for FIG. 2a. Delay volume 9 delays the arrival of the sample solution at capillary 7' such that the differential pressures substantially across capillaries 7 and 7' may be sensed by transducers 6 and 10 when capillary 7 contains sample material and capillary 7' contains only the solvent or reference fluid. Hence, the pressure drop sensed by transducer 6 will be different than the pressure drop sensed at that time by transducer 10 because transducer 10 will still be sensing a differential pressure associated with the pure solvent in capillary 7'. This enables the transducers to produce signals substantially corresponding to the pressure drops across a capillary containing pure solvent and a capillary containing the sample solution for use in determining relative viscosity, which may be mathematically related to other characterizations of the sample's properties, such as intrinsic viscosity, inherent viscosity, specific viscosity and reduced viscosity, by methods known in the art, such as is described in, for example, Abbott, et al and De Corral. The transducer signals may also be used in combination with the signals produced by a refractometer or similar concentration detector, which is part of a GPC system, to determine other information about the sample's properties such as molecular weight distribution.

After the relative differential pressure information is obtained, the fluid path diverter valve 8 may be switched to realign the valve, in a conventional fashion, such that the flow of fluid through capillary 7' is reversed as described for FIG. 2b to move the sample fluid in a direction from capillary 7' toward split junction 30 and fluid path diverter valve 8, through fluid path diverter valve 8, and then through fluid tube 11 to split junction 12. By switching fluid path diverter valve 8 in this manner, another relative differential pressure measurement may be taken of a new test sample flowing as per the configuration disclosed in FIG. 2b. Reversing the direction of flow through capillary 7' decreases or eliminates the unwanted breakthrough peak associated with the flow of the sample solution through that capillary, thus reducing the time needed for a successive analysis of another sample.

Figure 3A:
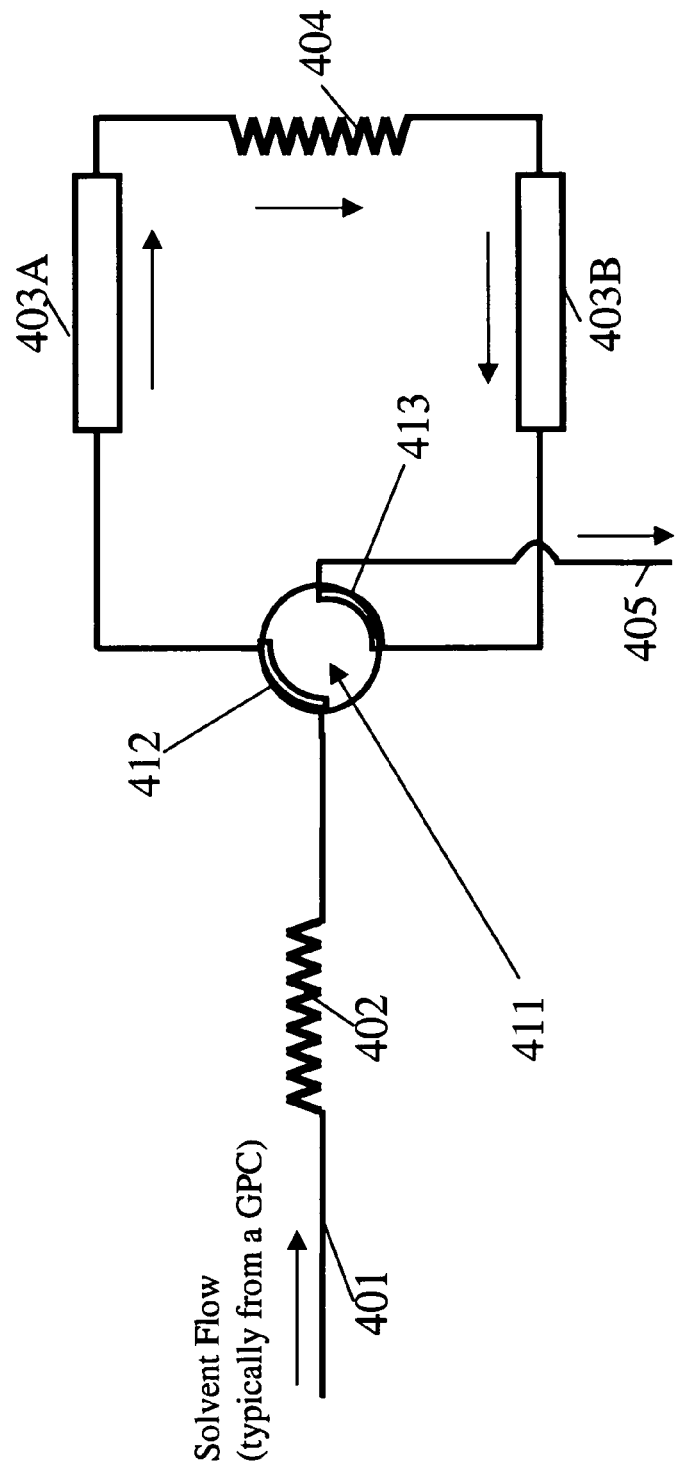
FIG. 3a is a block diagram of one embodiment of the subcircuit of the apparatus with two delay volume components and a fluid diverting component in orientation 'A'.
Figure 3B:
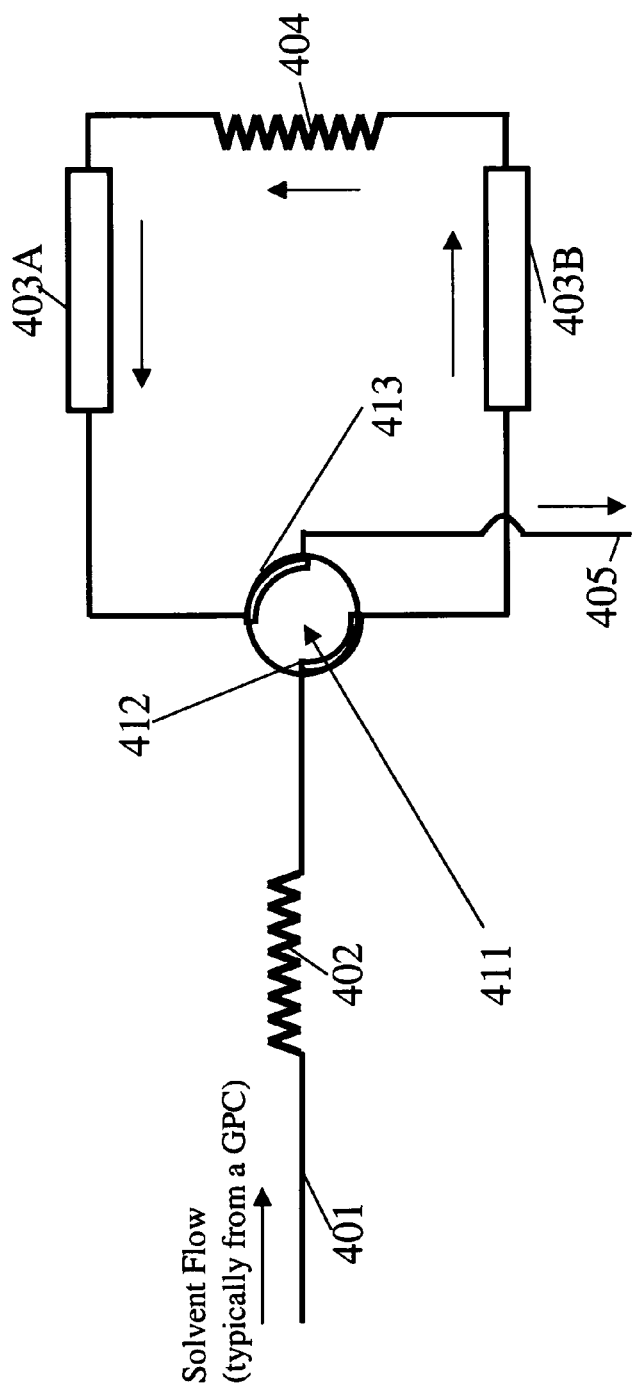
FIG. 3b is a block diagram of one embodiment of the subcircuit of the apparatus with two delay volume components and a fluid diverting component in orientation 'B'.

FIGS. 3a & 3b represent one embodiment of the subcircuit of the apparatus in alternative positions. A second 'delay volume component' 403B, is added to the viscometer flow-path after the 'reference capillary' 404. Additionally, a fluid diverting component 412 is included to select which of the two 'delay volume components' 403A and 403B is before and which is after the 'reference capillary' 404. Transducers may be arranged as known in the art for providing the pressure inputs to the transducer diaphragms, whereby the electrical signals provided by the transducers will be proportional to the differential pressure associated with the flow of fluid through the 'reference' capillary and/or the 'sample capillary' for use in the viscosity analysis. The calculation of relative viscosity may then follow that shown for the 2-capillary viscometer, equations 1-4.

FIG. 3a represents the one embodiment of the subcircuit in configuration 'A'. The fluid viscosity analysis circuit has an inlet tube 401 connected to a source of solvent flow (not shown) commonly used in the art. Inlet tube 401 connects to a capillary tube 402 known as the 'sample capillary', the other end of which is connected to a 'fluid diverting component' 411 (shown a 4-port, 2-position valve). The fluid pathway passes through the valve by way of a channel 412, thence onwards to the 'delay volume component A' 403A. The other end of the 'delay volume component A' is connected to the 'reference capillary' 404, the other end of which is connected to the 'delay volume component B' 403B. The other end of 'delay component B' is connected back to the 'fluid diverting component' 411 from which fluid in the delay component leaves the circuit through pathway 413 and exit tube 405.

FIG. 3b represents one embodiment of the subcircuit in configuration 'B'. The fluid viscosity analysis circuit is substantially identical to that described above for FIG. 3a except that the fluid diverting component 412 has been activated so that it is configured in its alternative position. Thus, the pathway from the entry point at tube 401 becomes: 'sample capillary' 402, 'fluid diverting component' 411, fluid pathway 412, 'delay volume component B' 403B, 'reference capillary' 404, 'delay volume component A' 403A, 'fluid diverting component' 411, fluid pathway 413, exit tube 405.

One method of operation is substantially as follows:

For the purposes of clarity and only to aid the understanding of the method, the starting configuration is assumed to be that shown in FIG. 3a. The instrument is in baseline mode when the fluid pathway has only solvent passing through it. Sample solution is injected or enters the circuit by way of tube 401. When it passes through 'sample capillary' 402, there will be a change in fluid pressure sensed by an appropriately placed 'transducer'. The simultaneous sensing of pressure across the 'reference capillary' 404, sensed by another appropriately placed 'transducer' (FIGS. 2a and 2b), will still be that due to the passage of solvent which is flowing from the 'delay volume component A' 403A. Thus the relative viscosity may be computed from the transducer signals as described in, for example, Haney, Abbott, et al. or de Coral. For example, when used in combination with a refractometer or similar concentration detector as the detection device of a gel permeation (or size exclusion) chromatograph, the transducer signals may also be used to determine other information about the sample's properties such as the molecular weight distribution or molecular size distribution.

The method of operation of the subcircuit in 3b is identical to 3a with the following changes.

As soon as the useful sensor data has been gathered, the 'fluid diverting component' 411 is activated, realigning the fluid pathways as shown in FIG. 3b. The effect of this is to reverse the position in the fluid pathway of the delay volume components '403A' and '403B' relative to the 'reference capillary' 404. Thus, the pathway from the entry point at tube 401 becomes: 'sample capillary' 402, 'fluid diverting component' 411, fluid pathway 412, 'delay volume component B' 403B, 'reference capillary' 404, 'delay volume component A' 403A, 'fluid diverting component' 411, fluid pathway 413, exit tube 405. Thus 'delay volume component B' 403B is in front of the 'reference capillary' and will provide the local supply of solvent to it. 'Delay volume component A' 403A is now downstream of the 'reference capillary'. Furthermore, the direction of flow of solvent through the 'delay volume component A' 403A is reversed and the sample solution that was passing through it is now flushed out by way of 'fluid diverting component' 411 and fluid pathway 413 to the exit pipe 405 where it will take no further part in the analysis process.

Thus, the fluid viscosity analysis circuit may be quickly made ready to accept a further sample for analysis. The fluid pathway may stay in this configuration for the duration of the analysis of the next sample, after which the fluid diverting component 411 may again be activated to align to the alternative configuration. By this time, the 'delay volume component A' will be completely replenished with solvent. There is minimal disturbance to the fluid viscosity analysis circuit other than the activation of the fluid diverting component and the consequent reversal of flow direction through a part of the circuit. Depending on the transducer connections, the reversal of flow through the 'reference capillary' may reverse the polarity of the pressure signal, but that effect can be accounted for in processing the transducer signals for a relative viscosity calculation.

Figure 4A:
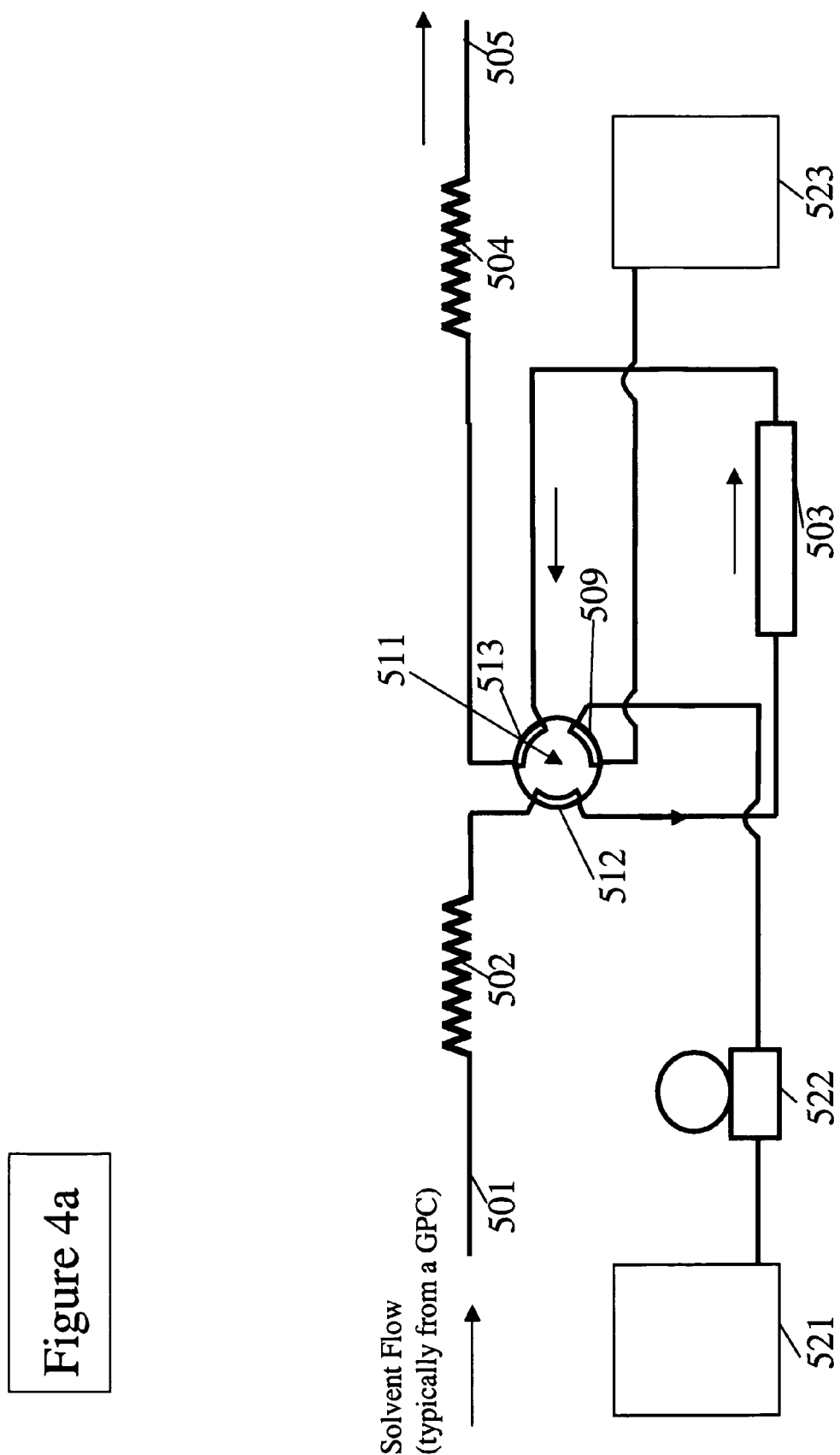
FIG. 4a is a block diagram of one embodiment of the subcircuit of the apparatus with a single delay volume component and a fluid diverting component in orientation 'A'.
Figure 4B:
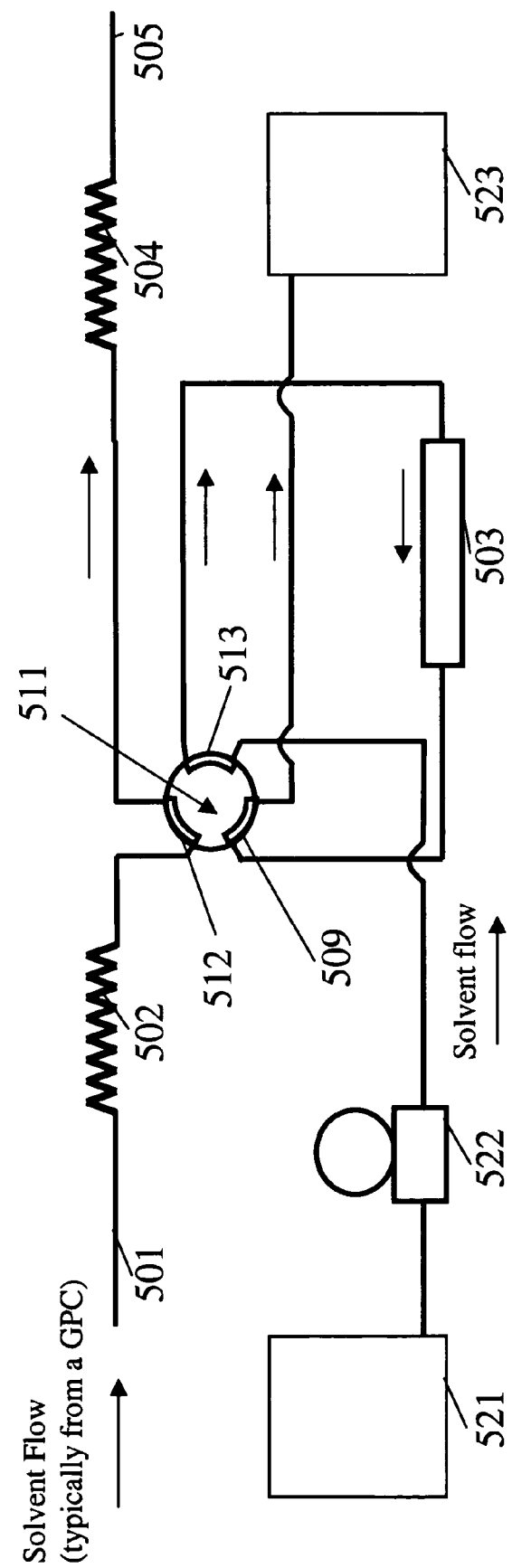
FIG. 4b is a block diagram of one embodiment of the subcircuit of the apparatus with a single delay volume component and a fluid diverting component in orientation 'B'.

FIGS. 4a & 4b represent a further embodiment of the apparatus containing a single 'delay volume component'. A further difference from the embodiments in FIGS. 3a and 3b is that the diverter 511 allows the 'delay volume component' 503 to be connected to either the viscosity measuring circuit or to an external flushing circuit.

FIG. 4a represents one embodiment of the apparatus in the 'configuration A'. The fluid viscosity analysis circuit has a tube 501 connected to a source of solvent flow but commonly used in the industry. Inlet tube 501 connects to a capillary tube 502 known as the 'sample capillary', the other end of which connects to one port of a 'fluid diverting component' 511 (as shown a 6-port, 2-position valve). The fluid pathway passes through the valve by way of channel 512, thence onwards to the 'delay volume component' 503. The other end of the 'delay volume component' is connected back to another port of the 'fluid diverting component' 511 and through channel 513 to a capillary tube 504 known as the 'reference capillary', the other end of which leaves the circuit by way of exit tube 505.

An external fluid circuit consists of a solvent source, the 'purge solvent reservoir' 521, connected to a 'solvent pump' 522, connected to the 'fluid diverting component', connected by way of channel 509 to the solvent waste vessel 523. The solvent reservoir 521 and the solvent waste vessel 523 may be the same as those used for the main viscometer circuit or can be separate, conventional units. The solvent pump 522 is typically not activated in this mode other than at start-up to dispel any air bubbles that may be present.

The embodiment of the apparatus as disclosed in FIG. 4a operates in, but is not limited to, substantially the following manner. The sample solution to be analyzed is injected, in the manner commonly known in the art, into the flowing stream of solvent passing through the viscometer circuit by way of inlet tube 501 through injection.

When the sample solution passes through 'sample capillary' 502, there will be a change in fluid pressure sensed by an appropriately placed 'transducer'. The simultaneous analysis of pressure across the 'reference capillary' 504, analyzed by another appropriately placed 'transducer', will still be that due to the passage of solvent which is flowing from the 'delay volume component' 503. The simultaneous sensing of pressure for each capillary allows the determination of relative viscosity as described in, for example, Haney, Abbott, et al. or de Coral. The transducer signals may also be used in combination with the signals produced by a refractometer or similar concentration detector as the detection system of a GPC or SEC to determine other information about the sample's properties such as molecular weight distribution.

FIG. 4b represents one embodiment of the apparatus in the 'configuration B'. After the pressure readings are obtained in the analysis configuration 'A', the fluid diverting component 511 may be switched to realign the valve, in a conventional fashion, such that the 'delay volume component' 503 becomes part of the external circuit, while solvent continues to flow in the main viscosity analysis circuit. In this embodiment, the 'solvent pump' 522 is activated to pump solvent through the external circuit by way of channel 513 of the fluid diverting component 511 and into the 'delay volume component' 503 leaving by way of channel 509 of the fluid diverting component 511 to the waste vessel 523 or alternative exit to waste. This way, the sample solution that was passing through the 'delay volume component' 503 is quickly flushed out to waste before it can pass through the 'reference capillary' 504 to cause a 'breakthrough peak'. When the 'delay volume component' 503 is again full of solvent, the 'solvent pump' is switched off and the fluid diverting component 511 may be switched to realign the valve. In this way, the regenerated 'delay volume component' 503 is restored to the analysis.

It may be seen from the preceding description that a new and improved system and method for analysis of fluid properties has been provided. Although very specific examples have been described and disclosed, the embodiments of one form of the apparatus of the instant application is considered to comprise and is intended to comprise any equivalent structure and may be constructed in many different ways to function and operate in the general manner as explained hereinbefore. Accordingly, it is noted that the embodiment of the new and improved system and method described herein in detail for exemplary purposes is of course subject to many different variations in structure, design, application, form, embodiment and methodology. Because many varying and different embodiments may be made within the scope of the inventive concept(s) herein taught, and because many modifications may be made in the embodiments herein detailed in accordance with the descriptive requirements of the law, it is to be understood that the details herein are to be interpreted as illustrative and not in a limiting sense.

What is claimed is:

1. A pressure sensing apparatus for obtaining signals for analyzing fluid samples, comprising:
   (a) a plurality of capillaries including at least one sample capillary containing a sample fluid; said plurality of capillaries further including at least one reference capillary containing a reference fluid;
   (b) at least one delay volume component connected in the same flow path as the reference capillary;
   (c) a valve operable to selectively alter a direction of fluid flow through at least one delay volume component;
   (d) at least one pressure transducer operable to sense a differential pressure associated with the flow of reference fluid through a capillary; and
   (e) at least one pressure transducer operable to sense a differential pressure associated with the flow of sample fluid through a capillary.

2. The apparatus of claim 1, wherein at least one pressure transducer is connected to permit a reference fluid to flow through said transducer.

3. The apparatus of claim 1, wherein at least one pressure transducer is connected to permit a sample fluid to flow through said transducer.

4. The apparatus of claim 1, wherein at least one pressure transducer is directly connected to opposite ends of a capillary for sensing a differential pressure associated with the flow of fluid through said capillary.

5. The apparatus of claim 1, wherein at least one pressure transducer is connected to sense a differential pressure associated with the flow of fluid through a capillary in combination with a differential pressure associated with the flow of fluid through a delay volume component.

6. The apparatus of claim 1, wherein at least one pressure transducer is connected to sense a differential pressure associated with the flow of fluid through a capillary in combination with a differential pressure associated with the flow of fluid through a valve operable to selectively alter a direction of fluid flow through at least one delay volume component.

7. The apparatus of claim 1 wherein said valve is operable to alter the direction of flow through said at least one reference capillary.

8. The apparatus of claim 1, wherein at least one capillary is connected to a fluid flow pat tat includes a GPC or SEC column set.

9. The apparatus of claim 1 further comprising: a pump for delivering reference fluid to said at least one delay volume component.

10. The apparatus of claim 1 further comprising: a reservoir for delivering reference fluid to said at least one delay volume component.

11. The apparatus of claim 1, wherein said plurality of transducers includes at least one transducer operable to sense a differential pressure associated with the flow of fluid through a reference capillary arranged in series with a sample capillary.

12. The apparatus of claim 1, wherein said plurality of transducers includes at least one transducer operable to sense a differential pressure associated with the flow of fluid through a reference capillary arranged in parallel with a sample capillary.

13. A method for sensing pressure for obtaining signals for analyzing fluid samples, comprising:
   (a) providing a plurality of capillaries including at least one sample capillary containing a sample fluid;
   (b) said plurality of capillaries further including at least one reference capillary containing a reference fluid;
   (c) introducing a flowing reference fluid to at least one reference capillary;
   (d) introducing a flowing sample solution to at least one sample capillary;
   (e) providing at least one delay volume component connected in the same flow path as at least one reference capillary;
   (f) providing a valve operable to selectively alter a direction of fluid flow through at least one delay volume component;
   (g) providing at least one pressure transducer operable to sense a differential pressure associated with the flow of reference fluid through a capillary; and
   (h) providing at least one pressure transducer operable to sense a differential pressure associated with the flow of sample fluid through a sample capillary.

14. The method of claim 13, further comprising: connecting at least one pressure transducer to permit a reference fluid to flow through said transducer.

15. The method of claim 13, further comprising: connecting at least one pressure transducer to permit a sample fluid to flow through said transducer.

16. The method of claim 13, further comprising: connecting at least one pressure transducer directly to opposite ends of a capillary for sensing a differential pressure associated with the flow of fluid through said capillary.

17. The method of claim 13, further comprising: connecting at least one pressure transducer to sense a differential pressure associated with the flow of fluid through a capillary in combination with a differential pressure associated with the flow of fluid through a delay volume component.

18. The method of claim 13, further comprising: connecting at least one pressure transducer to sense a differential pressure associated with the flow of fluid through a capillary in combination with a differential pressure associated with the flow of fluid through a valve operable to selectively alter a direction of fluid flow through at least one delay volume component.

19. The method of claim 13, further comprising: providing a GPC or SEC column set connected to a flow path that includes said at least one capillary.

20. The method of claim 13, further comprising: the step of providing a pump for delivering reference fluid to said at least one delay volume component.

21. The method of claim 13, further comprising: the step of providing a reservoir for delivering reference fluid to said at least one delay volume component.

22. The method of claim 13 further comprising: operating said valve to alter the direction of flow through said at least one reference capillary.

23. The method of claim 13 further comprising: providing at least one transducer operable to sense a differential pressure associated with a flow of fluid through a reference capillary arranged in series with a sample capillary.

24. The method of claim 13 further comprising: providing at least one transducer operable to sense a differential pressure associated with the flow of fluid through a reference capillary arranged in parallel with the sample capillary.

25. A sub-circuit for a system for sensing fluid pressure for analysis of fluid samples, including a multi-capillary viscometer comprising:
   (a) a plurality of capillaries including at least one sample capillary and at least one reference capillary;
   (b) a delay volume component connected in the same flow path as at least one reference capillary; and
   (c) a valve operable to selectively alter the direction of fluid flow through said delay volume component.

26. A pressure sensing apparatus for obtaining signals for analyzing fluid samples in a flow circuit containing a reference fluid, the apparatus comprising:
   (a) a plurality of capillaries,
   (b) at least one delay volume component in fluid connection with at least one capillary,
   (c) a valve for changing the direction of the fluid flow through at least one delay volume component,
   (d) at least one pressure transducer operable to sense a differential pressure associated with the flow of the reference fluid through at least one capillary, and
   (e) at least one pressure transducer operable to sense a differential pressure associated with the flow of a sample fluid through at least one capillary,
   such that the sample is engaged with at least one capillary and the differential pressure is sensed by the pressure transducer associated with each capillary for the determination of a characteristic of the sample fluid, the sample engages the delay volume component, the valve changes the direction of the fluid flow for purging the sample from the delay volume component and the circuit, the valve again changes the direction of the fluid flow through the delay volume component for the circuit to be charged with reference fluid and ready to receive another sample.

27. An apparatus for analyzing fluid samples in a flow circuit charged with a reference fluid comprising:
   (a) a first capillary for receiving fluid;
   (b) a second capillary for receiving fluid;
   (c) a delay volume in fluid connection with the capillaries;
   (d) a valve for changing the direction of fluid flow in the delay volume;
   (e) a pressure transducer operable to sense a differential pressure associated with the flow of fluid through the first capillary; and
   (f) a pressure transducer operable to sense a differential pressure associated with the flow of fluid through the second capillary,
   such that a sample is engaged with the first capillary and the differential pressure is sensed by the pressure transducer associated with each capillary for the determination of a characteristic of the sample fluid, the sample engages the delay volume, the valve changes the direction of the fluid flow for purging the sample from the delay volume and the circuit, the valve again changes the direction of the fluid flow through the delay volume for the circuit to be charged with reference fluid and ready to receive another sample.

28. A method for purging samples from a flow circuit for analyzing fluid samples comprising the steps of:
   (a) engaging the flow circuit with a reference fluid,
   (b) accepting a sample in the flow circuit,
   (c) sensing an attribute of the sample for determining a characteristic of the sample,
   (d) changing the direction of the flow of the sample in the flow circuit, and
   (e) purging the sample from the flow circuit such that the flow circuit is ready to accept another sample.

29. A method for purging samples from a flow circuit for analyzing fluid samples comprising the steps of:
   (a) engaging the flow circuit with a reference fluid,
   (b) accepting a sample in the flow circuit,
   (c) sensing an attribute of the sample for determining a characteristic of the sample,
   (d) changing the direction of the flow of the sample in the flow circuit,
   (e) purging the sample from the flow circuit,
   (f) accepting another sample in the flow circuit,
   (g) sensing an attribute of the sample for determining a characteristic of the sample,
   (h) changing the direction of the flow of the reference fluid in the flow circuit, and
   (i) purging the sample from the flow circuit such that the flow circuit is ready to accept another sample.

* * * * *